United States Patent [19]

Fergason

[11] Patent Number: 5,343,313
[45] Date of Patent: Aug. 30, 1994

[54] EYE PROTECTION SYSTEM WITH HEADS UP DISPLAY

[75] Inventor: James L. Fergason, Atherton, Calif.

[73] Assignee: James L. Fergason, Atherton, Calif.

[21] Appl. No.: 115,353

[22] Filed: Sep. 2, 1993

Related U.S. Application Data

[63] Continuation of Ser. No. 496,447, Mar. 20, 1990, abandoned.

[51] Int. Cl.$^5$ .................. G02F 1/1333; A42B 3/00; G02B 27/14
[52] U.S. Cl. .................. 359/83; 2/6.3; 345/8; 359/630
[58] Field of Search ......... 350/330, 331 R, 347 RVE, 350/352; 340/705, 980; 359/630, 900, 37, 40, 49, 93, 83; 2/6, 422, 6.1, 6.3, 6.4, 6.6; 345/7, 8

[56] References Cited

U.S. PATENT DOCUMENTS

| H686 | 10/1989 | Mullins | 350/352 |
|---|---|---|---|
| 3,787,109 | 1/1974 | Vizenov | 2/6 |
| 4,153,952 | 5/1979 | Dussich | 2/6 |
| 4,155,122 | 5/1979 | Budmiger | 350/331 R |
| 4,181,405 | 1/1980 | Cohen | 350/331 R |
| 4,462,661 | 7/1984 | Witt | 350/331 R |
| 4,527,691 | 3/1981 | Brooks | 351/158 |
| 4,560,239 | 12/1985 | Katz | 350/331 R |
| 4,688,900 | 8/1987 | Doane et al. | 350/347 V |
| 4,709,030 | 10/1987 | Petrzilka et a. | 350/350 R |
| 4,751,691 | 6/1988 | Perera | 351/158 |
| 4,759,608 | 7/1988 | Yang | 359/66 |
| 4,765,719 | 8/1988 | Fergason | 350/347 V |
| 4,808,978 | 2/1989 | Vernay | 340/705 |
| 4,813,767 | 3/1989 | Clark et al. | 350/341 |
| 4,867,551 | 9/1989 | Perera | 351/57 |
| 4,878,046 | 10/1987 | Smith | 359/630 X |
| 4,897,715 | 1/1990 | Beamon, III | 359/900 X |
| 4,900,133 | 2/1990 | Berman | 350/346 |
| 4,994,794 | 2/1991 | Price et al. | 340/980 X |
| 5,050,966 | 9/1991 | Berman | 359/630 X |
| 5,081,542 | 1/1992 | Efron et al. | 359/72 X |
| 5,097,352 | 3/1992 | Takahashi et al. | 359/63 |
| 5,172,256 | 12/1992 | Sethofer | 359/83 |

OTHER PUBLICATIONS

"Visor Problems", Approach, Published by the Naval Safety Center, Nas, (Norfold, Virginia), 1966, p. 23.
Sears et al., University Physics, 6th Edition, 1982, pp. 810–811.
Halliday et al., Physics, Part 2, 3rd Edition, 1978, pp. 1073–1075.
Moran, Apr. 1980, Integrated Military Displays and Controls.
Leon, IBM Technical Disclosure Bulletin, Projected Image Display, Vol. 22, No. 1, Jun. 1979.

Primary Examiner—William L. Sikes
Assistant Examiner—Ron Trice
Attorney, Agent, or Firm—Renner, Otto, Boisselle & Sklar

[57] ABSTRACT

A system for protecting the eyes of a wearer while permitting information to be conveyed to such eyes includes a first plane polarizer for selectively passing incident light or other electromagnetic energy toward such eyes as a function of a prescribed characteristic, such as polarization direction of such electromagnetic energy, a second plane polarizer for selectively passing incident light (electromagnetic energy) passed by the first polarizer toward such eyes as a function of a prescribed characteristic, such as polarization direction, of such electromagnetic energy, a means for changing such characteristic (i.e., polarization direction), as by rotation using birefringence or wave guiding, of such incident electromagnetic energy in response to a function (such as the intensity of the incident light) to effect a cooperation between the first and second polarizers to change a characteristic (reduce intensity or block light transmission) of such electromagnetic energy received by such eyes, and a heads up display for forming an image between the first and second polarizers to convey information to such eyes of such wearer independently of the operative mode of said changing means.

29 Claims, 4 Drawing Sheets

EYE PROTECTION SYSTEM WITH HEADS UP DISPLAY

This is a continuation of copending application Ser. No. 07/496,447 filed on Mar. 20, 1990 now abandoned.

TECHNICAL FIELD

The present invention relates, generally, as is indicated, to eye protection, and, more particularly, to apparatus for blocking high intensity electromagnetic energy, such as laser energy or that from an explosion, from the eyes of a person and/or from other devices. The invention relates, even more particularly, to the providing of eye protection in combination with a heads up display, and, especially, to a liquid crystal apparatus for blocking high intensity electromagnetic energy from the eyes of a person while permitting the full operation of the heads up display during protective blocking. The invention also relates to the combining of optical inputs; more particularly, in the case that at least one of those inputs is an object or real space and the other is an image; and even more particularly, wherein the inputs are combined to appear (visually, for example) spatially congruent.

In addition to the foregoing, the invention relates to a safety feature for use in aircraft and/or other vehicles to provide artificial information to enable or to facilitate operating of the aircraft and/or other vehicle during the period that the operator's eyes are being protected from specified electromagnetic energy.

BACKGROUND

Heads up display technology provides in the field of view of an individual, such as a pilot, a display of information, such as words, symbols, images, pictures, etc., while the pilot is viewing something else, such as the scene or view outside of an airplane. An advantage of a heads up display is that the pilot, or other individual using such heads up display, does not have to move his head to change the point of focus of his eyes, i.e., the main image being viewed by his eyes. In some instances the pilot may not even have to move his eyes while changing his point of focus.

Typically in a heads up display an image that contains specific information is projected ahead (forward) of the eyes of the viewer. If the viewer is wearing goggles, the goggles should not interfere with the projected image. Also, if the viewer is wearing a visor over a helmet or as part of a helmet, such visor should not interfere with the projected image. In some instances the visor is used both as a protective layer to block bright sunlight, for example, from the eyes of the viewer and also as a screen onto which the heads up display information can be projected for viewing by the viewer. Such projection may be by specialized cathode ray tube (CRT) projection apparatus, by holographic projection apparatus, or by other apparatus, which are known systems.

Various devices have been employed to protect the eyes from injury due to high intensity electromagnetic energy. One example is the liquid crystal apparatus disclosed in U.S. Pat. No. 4,765,719 by James L. Fergason. In the past other protection devices have been used in the goggles worn by a pilot, for example, to control and/or to minimize the intensity of and/or to block the electromagnetic energy transmitted toward the eyes of the pilot. A disadvantage with using eye protection in goggles in the past has been that the heads up display information which is projected outside of the goggles also is reduced in intensity or may even be blocked entirely from the pilot's eyes. Consideration has been given in the past to using means in the visor to provide eye protection from high intensity electromagnetic energy. Such a system would provide a variation in control of the transmitted light while still permitting the heads up display to be viewed through goggles from within the visor. However, the difficulty, complexity and cost of manufacturing such a large visor with eye protection light controlling characteristics are substantial, and reduced quality of viewing clarity through a complex visor system is envisioned.

Liquid crystal devices for controlling the transmission of light therethrough are known. One example is a twisted nematic liquid crystal apparatus. The twisted nematic liquid crystal apparatus includes a twisted nematic liquid crystal cell positioned between a pair of plane (linear) polarizers and selectively operable to rotate or not to rotate the plane of polarization of plane polarized light incident on the cell, e.g., as a function of whether or not a prescribed input, such as an electric field, is applied across the liquid crystal cell. Sometimes the twisted nematic liquid crystal cell is referred to as being operative to provide a wave guiding effect as light travels therethrough. If the two polarizers on the opposite sides of a twisted nematic liquid crystal cell are crossed, then light will be transmitted through such apparatus when the liquid crystal cell rotates the plane of polarization by ninety degrees or light will be blocked when the cell does not rotate the plane of polarization. Conversely, if such polarizers are parallel, then light will be blocked when the cell rotates the plane of polarization by ninety degrees and will be transmitted through the apparatus when the cell is not rotating the plane of polarization.

Other liquid crystal devices useful in controlling transmission of light are birefringent liquid crystal devices and optical retarders. An exemplary birefringent liquid crystal device, which also is or functions as a variable optical retarder, includes a liquid crystal cell that operates on the principle of birefringence and/or retardation to rotate or not to rotate the plane of polarization of incident polarized light. Such a birefringent liquid crystal device or optical retarder typically is positioned between a pair of polarizers, usually plane polarizers. The resulting optical effect, i.e., either blocking or transmitting of light, is a function of whether the polarizers are parallel or crossed and whether or not or the degree that the birefringent liquid crystal cell or optical retarder is rotating the plane of polarized light incident thereon. An example of a birefringent liquid crystal cell that provides variable optical retardation sometimes is referred to as a surface mode liquid crystal cell or device and is disclosed in U.S. Pat. Nos. 4,385,806, 4,540,243 and Re 32,521 by James L. Fergason. A birefringent liquid crystal cell/variable optical retarder also is shown in U.S. Pat. Nos. 4,566,758, 4,582,396 and 4,719,507. The speed of response of a birefringent liquid crystal device or variable optical retarder device, e.g., of the type disclosed in the mentioned patents, typically is faster than the usual speed of response for twisted nematic liquid crystal cells.

BRIEF SUMMARY OF THE INVENTION

The present invention relates to eye protection. It will be appreciated that although the preferred embodiment of the invention is directed to the protection of the eyes of a human being, the principles of the invention also may be used in connection with the protection of some other device, living or not, from electromagnetic energy. Therefore, when "eyes" are mentioned, it will be understood that other devices may be protected according to the invention, too.

The invention also relates to apparatus and methods for combining optical inputs. According to one aspect, two inputs can be combined while intensity (or some other characteristic) of each input can be controlled, preferably independently. According to another aspect, one input is an image and a second input is real space. According to a further aspect, the inputs are combined to appear spatially congruent. Preferably such optical inputs are electromagnetic energy representations thereof, such as light from an object in real space (so that the object can be seen by the human eye) and such as a projected image of another object, information, etc.

As it is used herein, the term electromagnetic energy means, broadly, the classical definition of electromagnetic energy or electromagnetic radiation. The subset of electromagnetic energy to which the invention more particularly, although not necessarily exclusively, applies is that electromagnetic energy which can affect the eyes (or some device), for example, enabling eyes to see or causing damage to the eyes, such as visible light, laser light or energy, ultraviolet and/or infrared light or energy, and so on. For convenience, the term light will be used to refer to all such electromagnetic energy that can be seen by the eyes or can otherwise affect the eyes; however, it will be appreciated that the invention may be employed equivalently or substantially equivalently with other forms and/or wavelengths of electromagnetic energy.

Also, although the invention is described in detail below with respect to the providing of protection for the eyes of a person from electromagnetic energy, such as that which may injure the eyes, it will be appreciated that the features of the invention may be employed to provide such protection for other devices and/or to control or to attenuate electromagnetic energy transmitted to such other devices.

Accordingly, the invention relates to a system for protecting the eyes of a person, including first means for selectively passing incident electromagnetic energy toward such eyes as a function of a prescribed characteristic of such electromagnetic energy, second means, separated or spaced apart from the first means, for selectively passing incident electromagnetic energy passed by the first means toward such eyes as a function of a prescribed characteristic of such electromagnetic energy, and changing means for changing such characteristic of such incident electromagnetic energy in response to a function to effect a cooperation between the first means and the second means to change a characteristic of such electromagnetic energy received by such eyes.

The invention more specifically relates to a system for protecting the eyes of a person, e.g. as is mentioned in the preceding paragraph, while permitting information to be conveyed to such eyes, including, further, means for forming an image between the first means and such eyes of such wearer to convey information to such eyes of such wearer independently or substantially independently of the operative mode of the changing means.

According to the present invention apparatus for protecting the eyes of an individual from injury due to high intensity electromagnetic energy is operative to provide such protection while still permitting the operation and viewing of a heads up display or the like.

According to an embodiment of the invention, an eye protection apparatus employs a liquid crystal cell between two polarizers. The liquid crystal cell is operative selectively or automatically to change a characteristic of light incident thereon, such as the plane of polarization of incident plane polarized light thereby to determine whether and/or to what extent light that impinges on the apparatus from outside the apparatus is attenuated or blocked prior to reaching the viewer's eyes. For compatibility with a heads up display, one of such polarizers is positioned relatively remotely from the viewer's eyes compared to the more proximate location at which the image of the heads up display image is projected or is formed. Therefore, when the liquid crystal cell is cooperative with the polarizers to block high intensity electromagnetic energy from a viewer's eyes, the heads up display still is viewable by the viewer.

According to an embodiment of the invention in which a heads up display is employed, means are provided to control, to adjust, to alter, to attenuate, etc., a characteristic of light, such as intensity of incoming ambient light or the like, independently or substantially independently of the display intensity.

In a preferred embodiment of the invention, the liquid crystal cell and one polarizer are mounted in goggles worn by the viewer, and the other polarizer is mounted on or is formed as part of the visor of a helmet worn by the viewer. Also, in an embodiment the visor may be partly metallized, e.g., silvered, on a surface, such as the inside surface more proximate the viewer's eyes, to provide a screen onto which the heads up display image may be projected without interfering with the light polarizing properties of the polarizer that is part of the visor or the light blocking properties of the eye protection apparatus.

According to an embodiment both glare reduction and intensity control may be provided in an eye protection apparatus.

According to an embodiment both glare reduction and intensity control may be provided in an eye protection apparatus with a heads up display.

According to an embodiment substantially complete control of intensity of transmitted electromagnetic energy is provided for use in a heads up display system substantially independently of the heads up display.

According to another embodiment automatic control of electromagnetic energy, such as light, intensity is provided in connection with a heads up display system substantially independently of heads up display.

In a broad sense the invention provides means for merging two images (or the like, such as scenes, information, and so on) in the same space, while permitting independent control of a function of a least one image, such as the intensity thereof.

According to an embodiment two (or more) optical inputs are superimposed to be spatially congruent. Preferably the superimposed inputs are combined to appear overlapping in the same location or space. Preferably one input is an object in real space, real space itself, etc., especially as it appears to the human eye, and a second input is an image. Moreover, preferably such combining or superimposing of optical input is accomplished while permitting independent control of intensity (or some other characteristic) of each input.

Further, preferably the inputs are placed in such a way as to appear at infinity relative to a human eye. Typically infinity in such a case is approximately more than about ten to thirty feet (or possibly as much as about fifty feet) away from the viewer (eye), thereby enabling and/or facilitating the eye to focus simultaneously on both optical inputs.

According to the preferred embodiment, which is described in detail, one image is a scene outside an aircraft (or other vehicle) and the other is the information provided by a heads up display.

It will be appreciated that images and the like from other sources may be merged, combined, etc., and controlled according to the invention.

In addition to the foregoing, the invention relates to a safety feature for use in aircraft and/or other vehicles to provide artificial information to enable or to facilitate operating of the aircraft and/or other vehicle during the period that the operator's eyes are being protected from specified electromagnetic energy.

The foregoing and other objects, features and advantages of the invention will become more apparent as the following description proceeds. Although several embodiments of the invention are described, it will be appreciated that the scope of the invention is to be determined by the scope of the claims hereof.

To the accomplishment of the foregoing and related ends, the invention, then, comprises and features hereinafter fully described in the specification and particularly pointed out in the claims, the following description and the annexed drawings setting forth in detail a certain illustrative embodiment of the invention, this being indicative, however, of but one of the various ways in which the principles of the invention may be employed.

It will be appreciated that although several embodiments are shown here, features from one embodiment may be employed with a different embodiment.

DETAILED DESCRIPTION

Figure 1:
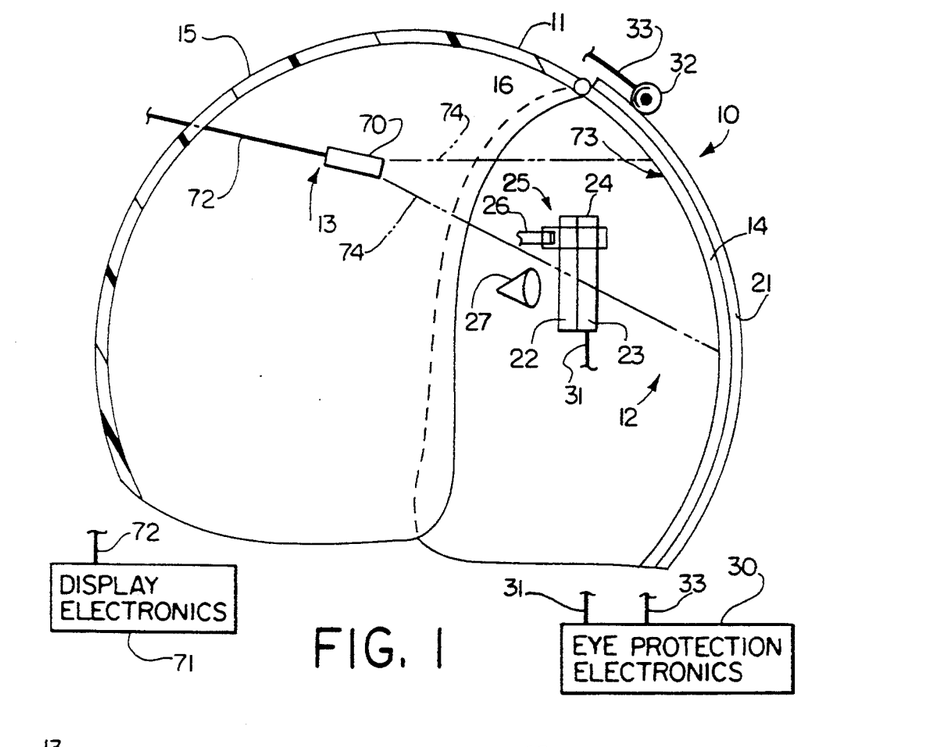
FIG. 1 is a schematic illustration of an eye protection apparatus used in a helmet with a heads up display in accordance with the present invention.

Referring, now, in detail to the drawings, wherein like reference numerals designate like parts in the several figures, and initially to FIG. 1, a combination helmet, eye protection apparatus, and heads up display system is designated 10. The system 10 includes a helmet 11, eye protection apparatus 12, and heads up display apparatus 13. The system 10 may be worn by a person, such as a pilot of an aircraft, by placing the helmet 11 on or over the head. The eye protection apparatus 12 is intended to protect the eyes of such person from high intensity electromagnetic energy, such as a high intensity beam from a laser, some other bright flash, such as that produced by an explosion, etc. The eye protection apparatus 12 also may be used to control or to attenuate ambient light intensity reaching the eyes; moreover, such control (which also includes attenuation, as it is used herein) may be provided substantially independently of the heads up display or operation of the heads up display. The heads up display apparatus 13 may be a conventional one that is able to display images representing certain information in the field of view of the person wearing the helmet. The system 10 also is intended to provide the other usual protective oxygen or air supply and other functions of a helmet.

The eye protection apparatus 12 is described hereinafter with respect to the protecting of the wearer's eyes from light that has a relatively high intensity characteristic, for example, by blocking transmission of at least some, and preferably all, of such light to the wearer's eyes. However, it will be appreciated that the features of the invention may be used to protect the eyes of the wearer from light that has a prescribed wavelength characteristic or some other characteristic or condition from which protection is desired, to protect the eyes from other types of electromagnetic energy (also sometimes referred to and including electromagnetic radiation) such as that from a laser, from an explosive flash, and so on. Thus, it will be understood that reference to light hereinafter means all other forms of electromagnetic energy with respect to which the invention may be employed to provide the desired protection. Also, while the eye protection apparatus 12 preferably is used to protect the eyes of a human being, it also may be employed for protecting eyes of animals, and for otherwise protecting human beings, animals and other objects (animate or inanimate) from specified electromagnetic energy.

The helmet 11, which may be worn on the head of a person, includes a front visor 14 and a head piece 15. The visor 14 is primarily for protectively covering the face and eyes of the wearer while allowing the wearer still to see out through the visor. The visor may be transparent. The visor 14 may be tinted to reduce the intensity of electromagnetic energy (light) reaching the wearer's eyes. Further, the visor 14 may be semi-transparent, e.g., having a partially reflecting coating of a reflecting material, such as silver or gold, thereon, as is well known. The visor 14 may be attached to the head piece 15 by a hinge 16 enabling the visor to be rotated (pivoted, tilted or the like) out of the way of the user's field of view. The head portion or head piece 15 is primarily for covering and protecting the head of the wearer. Various communication apparatus, such as radio speakers and microphones, for example, may be included in the helmet. Also, various breathing apparatus, such as part of an oxygen supply system, may be included in the helmet. Other than the portions of the helmet specifically described herein, the various portions of the helmet may be of conventional design typically used in a helmet for an aircraft pilot or the like. Typically the head piece 15 and the visor 14 of a conventional helmet are made of plastic or other synthetic materials, and this, too, preferably is the case for the present invention.

The eye protection apparatus 12 primarily includes three parts, as follows: a first member 21 for selectively passing incident electromagnetic energy toward the wearer's eyes as a function of a prescribed characteristic of such electromagnetic energy; a second member 22 for selectively passing incident electromagnetic energy passed by the first member toward the wearer's eyes as a function of a prescribed characteristic of such electromagnetic energy; and a device 23 for changing a characteristic of such incident electromagnetic energy in response to a function to effect a cooperation between the first member and the second member to change a characteristic of such electromagnetic energy received by the wearer's eyes.

In the preferred embodiment the characteristics mentioned in the preceding paragraph are the directions of plane polarized light; the function is light intensity; and the first and second members 21 and 22 are respective polarizers, more particularly plane (sometimes referred to as linear) polarizers. A plane polarizer passes light that has an electric vector in a particular direction so that the passed or transmitted light is referred to as plane (or linearly) polarized light. The plane polarizer ordinarily tends not to pass light that has an electric vector orthogonal to the mentioned particular direction. According to the invention, though, the first member 21 may be another type of polarizer, such as an elliptical polarizer or a circular polarizer, or the first member 21 may be some other type of device which is cooperative with the second member 22 to provide the desired protection described herein.

Also, although in the preferred embodiment the second member 22 is a polarizer, more particularly a plane polarizer, the second member 22 may be another type of polarizer, such as an elliptical polarizer or a circular polarizer, or the second member may be some other type of device. The second member 22 is intended to cooperate with the first member 21, as determined by the changing device 23, to provide the desired protection, such as light attenuation or blocking of light transmission to the eyes of the wearer.

According to the preferred embodiment and best mode of the invention, then, the first member 21 is a plane polarizer attached either to the inside surface or the outside surface of the visor 14 or the visor 14 itself may be a plane polarizer. Plane polarizers are well known devices. They may be formed of flexible material that fits in intimate engagement with a surface of the visor 14. If the visor 14 itself is a plane polarizer, it may be curved in conventional fashion.

According to the preferred embodiment and best mode, the second device 22 is a plane polarizer which is the lens or part of the lens of a goggle-type device 25. Further, according to the preferred embodiment, the changing device 23 is a variable optical retardation device, more preferably liquid crystal device or liquid crystal cell 24 of the birefringent type, and still more preferably a relatively high speed surface mode type of birefringent liquid crystal device. Preferably the changing device 23 also is incorporated in the mentioned goggle-type device 25. Such goggle-type device 25 is able to be mounted by a conventional strap 26 to the head of a wearer to position the second member 22 and the changing device 23 in front of the eyes 27 of the wearer, particularly between the eyes and the first member 21. The second member 22 and the first member 21 are spaced apart so that what may occur optically (such as the occurrence or projection of an image from the heads up display 13) therebetween will not be blocked by the cooperative effect of such first and second members from reaching the eyes 27, as is described further below.

The eye protection apparatus 12 also includes electrical and/or electronic circuitry 30, which is operable via a connection 31 to the changing device 23 to operate and/or to control the changing device. Such operation, for example, may cause rotation of the plane of polarization of light incident on the changing device 23 or may cause non-rotation of such plane of polarization. Moreover, the electronics 30 and changing device 23 may be cooperative to effect such rotation by 90 degrees or by more or less than 90 degrees, as may be desired. The amount of such rotation may be determined, for example, as a function of the magnitude of voltage or electric field applied to the liquid crystal in the changing device 23, as is described in a number of the above-mentioned patents or as a function of some other input. The amount of rotation, too, may be a function of the particular wavelength of light desired to be blocked or transmitted.

A sensor 32, such as a photocell, photodetector, photosensitive diode, etc., also may be included as part of the eye protection apparatus 12. The sensor 32 is positioned to receive and to sense electromagnetic energy that is incident thereon and would tend to be incident on the eyes 27. The sensor 32 may be mounted on the helmet 11 or may be positioned elsewhere to provide the desired function of sensing incident electromagnetic energy or at least a characteristic thereof. Such a characteristic ordinarily would be that or would represent that from which protection of the eyes 27 is desired by the eye protection apparatus 12. Accordingly, a connection 33 is provided from the sensor 32 to the eye protection electronics 30, which in turn operates the changing device 23 to cause light to be transmitted or blocked relative to eyes 27.

Figure 2:
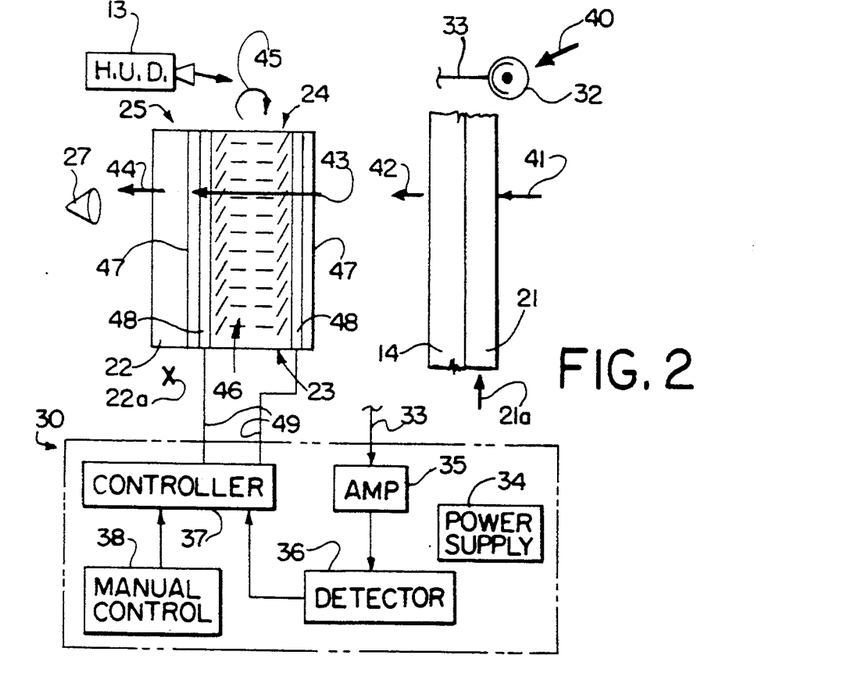
FIGS. 2 and 3 are schematic illustrations of one embodiment of the invention using a surface mode liquid crystal device, respectively, in light transmitting and light blocking modes.
Figure 3:
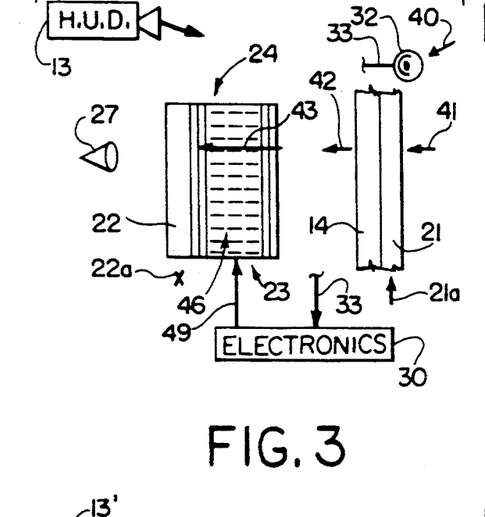

Exemplary operation of the eye protection apparatus 12 is described with respect to FIGS. 1, 2 and 3. As is shown, the first member 21 is a plane polarizer, which has a polarization direction that is vertical and is in the plane of the drawing, as is represented by arrow 21a. Also, as is shown, the second member 22 is a plane polarizer, the direction of polarization being identified by a letter "X" 22a which represents an arrow pointing into the plane of the drawing so as to be crossed relative to the direction of polarization 21a of the first plane polarizer 21. Therefore, absent the changing device 23, the crossed polarizers would cooperate to tend to block transmission of light, as, of course, is known.

As is seen in FIG. 2, the electronics 30 includes a power supply 34, an amplifier 35, a detector circuit 36, and a controller circuit 37. The electronic circuitry (referred to as "electronics" for convenience) 30 also may include a manual control 38, for example, as a potentiometer or the like for manually controlling and/or adjusting the intensity of light transmitted to the viewer's eyes 27.

The power supply 34 may be a conventional power supply providing power to the various other portions of the electronics 30 to operate in the manner described herein. The amplifier 35 is coupled via the connection 33 to the sensor 32. The amplifier 35 amplifies the output from the sensor 32, such output being representative of a characteristic of electromagnetic energy 40 (e.g., light intensity) incident on the sensor 32. The detector 36 may be a conventional voltage level detector or threshold detector circuit, which responds to the output from the amplifier 35. Depending on whether the intensity of light 40 exceeds a prescribed threshold level or does not exceed such threshold level, the detector 36 will operate a controller 37 (such as a controlled electronic amplifier) that in turn determines the nature of the electrical input (if any) to the changing device 23.

If the intensity of light 40 is below a prescribed threshold level, then the changing device 23 is allowed to or is caused to operate in a fashion so that incident light 41 impinging on the first polarizer 21 and transmitted therethrough as plane polarized light 42, will be rotated, say a full 90 degrees, by the changing device 23, and will pass all the way through the goggles 25 (including through the changing device 23 and second polarizer 22) to the eyes 27, as is shown by arrows 43 and 44 in FIG. 2. Curled arrow 45 in FIG. 2 indicates that such rotation of plane of polarization is occurring in the changing device 23. However, if the intensity of light 40 exceeds a threshold level, e.g., intense laser light, then the controller 37 in the electronics 30 is cooperative with the changing device 23 to allow and/or to cause the changing device not to rotate the plane of polarization of the plane polarized light 42 received thereby so that the plane polarizer 22 will block transmission of such light, which is represented by arrow 43 in FIG. 3, from reaching the eyes 27.

If desired, the amplifier 35 and controller 37 may be coupled directly (or via the detector 36) to effect rotation of the plane of polarization an amount more than zero and less than 90 degrees, e.g., depending on the voltage of the electric field supplied to the liquid crystal device 24 thereby, as a function of the intensity, etc., of light impinging on the sensor 32 so that the intensity of light transmitted through to the eyes 27 is attenuated but the light is not entirely blocked. The manual control 38 may be any of a variety of devices, circuits, etc. The manual control may be adjusted manually by the viewer to control intensity of light 44 reaching eyes 27; alternatively, some other means may be used to adjust the control 38, e.g., as a function of something other than the light sensed by the photosensor 32. Accordingly, the manual control 38 may be a potentiometer, an amplifier circuit, etc., that can affect the controller 37 or some other part of the electronics 30 or of the sensor 32 to alter the condition of the changing device, e.g., increasing or decreasing voltage to increase or to decrease rotation of polarization. Other types of manual controls also may be used for the desired purposes or other purposes in association with the invention.

The birefringent liquid crystal device or cell forming the changing device 23 includes operationally nematic liquid crystal material 46 located in a volume defined between a pair of generally parallel transparent plates 47. The plates 47 may be of glass, plastic or other material. Electrodes 48 on the surfaces of the plates are energized by the controller 37, e.g., receiving a voltage thereacross, to establish an electric field across the liquid crystal material 46 located between the plates 47. A seal (not shown) between the plates retains the liquid crystal material 46 in the space between the plates. The surfaces of the plates facing inside the liquid crystal cell are treated to cause or to influence a preferred alignment of the structure (or directors) of the liquid crystal material in the cell. Such surface treatment causes a preferred alignment of the liquid crystal material at and proximate the surfaces to be generally aligned parallel (or at a slight tilt angle but still generally parallel) with respect to the surfaces and so that the alignment direction of liquid crystal material at one surface is the same as the alignment direction of the liquid crystal at the other surface, although the tilt angle may be the same or different. The direction of alignment of the liquid crystal material at the surfaces preferably is at about an angle of 45 degrees relative to the direction of polarization of the plane polarizer 21 to optimize the birefringent effect.

Preferably an electrical bias, another bias technique, or some other means retains or is operative to retain the alignment of at least some of the liquid crystal material, which is located deeper in the liquid crystal cell between the plates and, thus, less proximate the surfaces of the plates 47, to be approximately perpendicular with respect to such plates. Then, when an appropriate electric field, e.g., one of sufficient magnitude, is applied by the electrodes across the liquid crystal material, the liquid crystal material proximate the surfaces tends to realign so as to become generally perpendicular to the surfaces, as is shown in FIG. 3.

By maintaining such alignment the liquid crystal material deeper in the cell relative to the surfaces, the cell can operate in a so-called surface mode manner, e.g., as is described in the above-referenced U.S. Pat. Nos. 4,385,806, 4,540,243, Re 32,521, 4,566,758, 4,582,396, and 4,719,507. Also, maintaining such alignment (or at least maintaining a semblance of such alignment) provides operation such that primarily optical switching action during use occurs mostly at or proximate the surfaces of the liquid crystal cell or light modulator, and this also provides both fast operation and optical uniformity across the field of view.

When most of the liquid crystal material is aligned perpendicularly to the surfaces as is illustrated in FIG. 3, light travels along the ordinary axis of the liquid crystal material, and therefore no retardation occurs. When the liquid crystal material is aligned parallel to the surfaces, retardation occurs as light travels relative to the extraordinary axis of the liquid crystal material which exhibits birefringence. The amount of retardation will depend on the magnitude of such birefringence, the thickness of the layer of liquid crystal material proximate the surfaces of the liquid crystal cell changing device 23, and the wavelength of the transmitted light.

According to a preferred embodiment the thickness of the surface mode birefringent liquid crystal cell or device 24 is a whole number multiple of one half the wavelength of green light, which has a wavelength of 550 nm. Such wavelength is that at which there ordinarily is high visual acuity. Therefore, when the apparatus 10 is not blocking light, a substantial amount of light from outside the helmet 11 will be transmitted to the viewer's eyes 27 for viewing. When in light blocking mode, such preferred embodiment provides an odd whole number multiple of ¼ wavelength retardation (and, thus, an odd whole number multiple of 90 degrees rotation of polarization) for such green light to maximize the light blocking effectiveness relative to the high green visual acuity of the eyes 27 while also providing substantial blocking of other wavelengths. If desired, operation at and/or about other wavelengths also may be selected by changing the indicated characteristics of the liquid crystal device 24.

Briefly, the birefringent surface mode liquid crystal cell or device 24, which forms the changing device 23 operates as follows: When the intensity of light 40 incident on the sensor 32 is less than a prescribed level, the controller 37, which is coupled via electrical leads 49 to electrodes 48, causes the liquid crystal to assume an alignment that provides a prescribed amount of relative retardation of the ordinary and extraordinary rays of the plane polarized light incident thereon thereby to rotate the plane of polarization preferably by 90 degrees. Such alignment of the liquid crystal material 46 in the liquid crystal device 24 finds some of the liquid crystal material, namely, that near the surfaces of the plates 47 and electrodes 48, oriented in a direction that is generally parallel to the plates and also finds some of the liquid crystal material that is located deeper into the interior of the cell relatively more remote from the electrodes 48 to be aligned generally in a direction more perpendicular with respect to the surfaces of the electrodes and plates 47. Since the polarizers 21 and 22 are crossed and the plane of polarization of the polarized light 42 is rotated, e.g., by 90 degrees, rotated polarized light 43 is transmitted through the second polarizer 22 as light 44 which passes to the eyes 27.

However, when the intensity of the light 40 incident on the sensor 32 exceeds a prescribed value, the electronics 30 is operative to provide adequate voltage across the electrodes 48 and, thus, electric field across the liquid crystal material 46 to cause at least some, if not all, of the liquid crystal near the surfaces to align relative (preferably in parallel) to the electric field; the liquid crystal material in the central part of the liquid crystal cell or device 24 remains aligned in parallel with the field. As a result, the amount of the aforementioned retardation is reduced and the rotation of plane of polarized light is reduced, preferably is eliminated. Accordingly, incident light 41 will be polarized by the first polarizer 21 as light 42, and such light will pass as light 43 through the changing device 23 (without rotation) and to the second polarizer 22 at which the light is blocked from the eyes 27.

Further detailed explanation of operation of a birefringent surface mode-type of liquid crystal device for controllably rotating the plane of polarization of light incident thereon is presented in the aforementioned patents, the disclosures of which hereby are incorporated by reference.

If desired, additional optical parts, such as quarter wave plates, or the like, may be included in the optical path of light 41, 42, 43, 44, e.g., to provide compensation for improving angle of view (an example being disclosed in U.S. Pat. No. 4,385,806) and/or for other purposes. Also, as will be appreciated, manual adjustment of the manual control 38 can be used to alter intensity of light transmitted through to the eyes 27 independently of and/or cooperatively with the sensor 32 and other portions of the electronics 30.

From the foregoing, then, it will be appreciated that the eye protection apparatus 12 is operative under one set of conditions to allow light and images from a source that is external of the helmet to be transmitted through to the eyes 27 and under a different set of conditions, such as the occurrence of incident electromagnetic energy exceeding a prescribed threshold level, to protect the eyes 27 by blocking such excessive electromagnetic energy from reaching the eyes. The foregoing is accomplished while still maintaining operability of the heads up display apparatus 13. Therefore, while light is transmitted by the eye protection apparatus 12 and even while the eyes are protected by the eye protection apparatus 12 from excessive electromagnetic energy that is occurring outside the helmet 11, images projected by the heads up display 13 still can be viewed. Those images projected by the heads up display 13 may be used to enable and/or to facilitate the pilot in controlling an aircraft or equipment associated with the aircraft, and so on.

The illustrated exemplary heads up display 13 includes a projector device 50, display electronics 51 appropriately coupled as by connection 52 to the projector 50, and a surface or screen area or space 53 onto which an image or information can be projected by the projector 50. The projector 50 may be, for example, a conventional cathode ray tube (CRT) projector-type of device typically used in a heads up display. The projector 50 preferably is located partly or entirely within the head piece 15 of the helmet 11. As it is seen in FIG. 1, the projector 50 is located within the head piece 15 in position to project an image bounded by dashed lines 54 past the wearer's head inside the helmet so that the image can be formed in the space on the surface area 53, for example, on the inside surface of the visor 14. Such inside surface may include a material thereon to facilitate forming an image of desired quality preferably without substantially interfering with the ability of the eyes 27 to view through the visor 14 to the environment that is external of the helmet 11. It will be appreciated that means other than a projector type of device may be used to produce the desired heads up display of information to the wearer of the helmet 11.

Since the polarizers 21 and 22 are spaced apart from each other and since the image from the heads up display 13 is formed between the polarizers 21 and 22, operation of the eye protection device 12 to block light emanating from outside the helmet 11 from reaching the eyes 27 or to transmit such light to the eyes 27 will not interfere with the ability of the eyes 27 to view the image formed at the space or area 53 by the heads up display 13.

In a broad sense images, information, etc. emanating from different sources, e.g., the sources being at different sides of the space 53, can be viewed at, proximate, and/or relative to the space 53. Also, a characteristic, such as intensity, of the image, information, etc., emanating on one side of the space, such as light 41, can be controlled at the other side of the space; and preferably such control can be achieved independently or substantially independently of the images, information, etc., emanating at such other side of the space 53. In the preferred embodiment, the images emanating outside the helmet 11, visor 14 and space 53 can be combined with information developed by the heads up display inside the helmet 11; and the intensity of the outside image can be controlled or attenuated by the eye protection apparatus 12.

In general, then, it will be appreciated that the invention broadly provides for the combining of plural optical inputs; preferably those inputs are from two sources; and more preferably, a first input is a view into real space wherein an object, for example, can be seen and a second input is an image developed by an imager. In one example, the image is created by a heads up display projection system; but it will be appreciated that other techniques can be used to provide such image. It also will be appreciated that the source of the first input may be other than a scene, view or object in real space, for example, such source may be another projector, projected image, or something else.

The invention provides the ability to combine two optical inputs such that the intensity or some other characteristic of at least one and preferably both of the optical inputs independently of the other. Adjustment of the first input may be accomplished, for example, as a function of the surface mode liquid crystal cell or birefringent liquid crystal cell or variable optical retarder described herein. Adjustment of the second input may be accomplished, for example, by adjustment of the output of the heads up display projector. It will be appreciated that other means also may be employed to adjust intensity or some other characteristic of each of the inputs that are combined by the invention.

The two images that are combined in the invention are effectively superimposed. They are superimposed in real space. In the preferred embodiment, the two inputs are combined is such a way that the inputs appear spatially congruent, and they are overlapping in the same location. Thus, the optical inputs are combined to appear in the same spatial relation, e.g., spatially congruent or overlapping. Moreover, in the preferred embodiment, the two optical inputs, or at least the effective images thereof, are placed by the invention or result in being or appearing effectively at infinity relative to what the human eye would perceive effectively as infinity. More specifically, the focus of the human eye on objects or images that are approximately from about ten to thirty, or perhaps fifty, feet away approximately the same, and such is considered relative infinity for such eye. In the present invention it is possible to cause the heads up display to project an image such that the image appears effectively at infinity to the viewing eye. The image in real space which forms the first optical input of the present invention also is approximately at infinity. Therefore, it is quite easy for the human eye to focus simultaneously on both of the superimposed portions of the scenes, images, etc. being viewed in accordance with the present invention.

Glare reduction is another feature of the present invention. Glare often interferes with vision due to excessive glare brightness to which the eyes adjust (closing or contracting the iris), thus reducing eye sensitivity to less bright light or images. Light that is a result of glare usually is due to reflection from an object, such as a flat metal object, water, glass, snow, etc., and such glare light usually has a dominant plane polarization characteristic. In fact, the direction of such dominant plane polarization characteristic tends to be in a horizontal plane, that is, generally orthogonal to the direction of incident light. By using a vertical orientation for the polarization direction or axis of polarization of the input polarizer 21 of the eye protection apparatus 12 in the apparatus 10 of the invention, the intensity of light due to glare reaching the eyes 27 tends to be reduced due to the blocking effected by that input polarizer.

Figure 4:
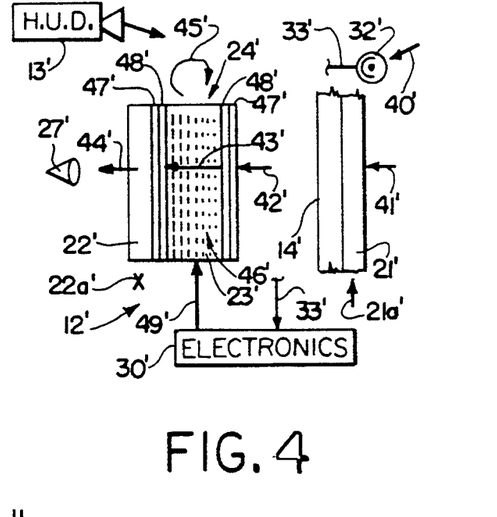
FIGS. 4 and 5 are schematic illustrations of a second embodiment of the invention using a twisted nematic liquid crystal device, respectively, in light transmitting and light blocking modes.
Figure 5:
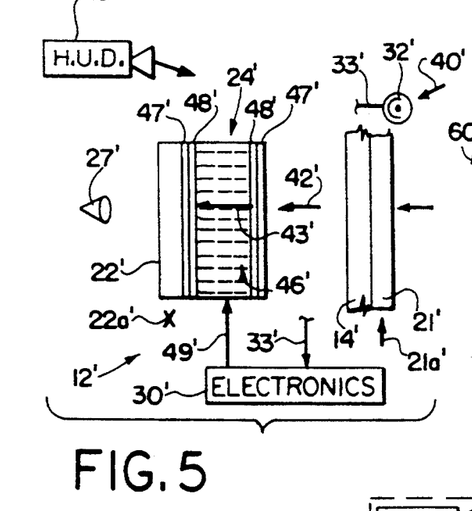

In FIGS. 4 and 5 an alternate embodiment of the eye protection apparatus 12' which uses a twisted nematic liquid crystal cell or device 24' of the changing device 23' instead of a birefringent liquid crystal cell (described above) is illustrated. Parts in FIGS. 4 and 5 that correspond with parts shown in FIGS. 1 through 3 are identified by the same reference numerals modified with a prime identifier. The eye protection apparatus 12' includes first and second plane polarizers 21', 22', which are oriented such that their polarization axes are crossed. Accordingly, arrow 21a' indicates the polarization direction of the first polarizer 21' being in the plane of the drawing and pointing in a vertical direction. The polarization axis 22a' is pointing into the plane of the drawing, as is represented by the crossed lines designated 22a'. Therefore the first and second polarizers 21', 22' are crossed at 90 degrees relative to each other. Incident light 41' is transmitted through the first polarizer 21' and visor 14' as polarized light 42'. As the light 42' is transmitted through the twisted nematic liquid crystal cell or device 24' of the changing device 23', the plane of polarization thereof is rotated by 90 degrees as is represented by the curved arrow 45', and light 44' then is transmitted to the eyes 27' via the second polarizer 22'. Such rotation sometimes is referred to as the wave guiding effect as opposed to the birefringent retardation effect described above. Transmission occurs when the light 40' incident on the sensor 32' is below a prescribed intensity so that the electronics 30' does not cause any change in the twisted alignment of the liquid crystal material 46' within the twisted nematic liquid crystal cell or device 24' of the changing device 23'.

However, when the intensity of incident electro-magnetic energy 40' exceeds a prescribed threshold level, the same is sensed by the sensor 32' and is detected by the electronics 30', which in turn applies suitable electric field across the liquid crystal material 46' to cause the same to align relative to that field. The aligned liquid crystal material 46' no longer rotates the plane of polarization of the light 42' incident thereon. Therefore, the light 43' is blocked by the second polarizer 22' from reaching the eyes 27'.

It is noted here that the polarizers 21 and 22 (also meaning polarizers 21' and 22') may ordinarily be relatively oriented in parallel or crossed relation depending on whether, when the changing device rotates the plane of polarized light, light is to be blocked or transmitted. If some residual rotation occurs even though the changing device 23 (also meaning the changing device 23') is not intending to produce maximum rotation, a minor adjustment in the relative alignment of the polarizers 21 and 22 may be provided. Further, it will be appreciated that although the first and second members 21 and 22 are described as plane polarizers and the changing device 23 as a device for rotating the plane of polarization, the first and second members may be other types of devices and the changing device may be another type of device that is selectively operable to cause the first and second members to cooperate for blocking or not blocking the transmission of light, preferably without interfering with operation of the heads up display. Examples of other changing devices useful in the invention include thin birefringent liquid crystal cells or devices, so-called pi cells or devices, so-called supertwist liquid crystal cells or devices, and other non-liquid crystal devices or liquid crystal devices that can be controlled to alter a characteristic of light to effect the desired light-blocking or attenuating of light.

Figure 6:
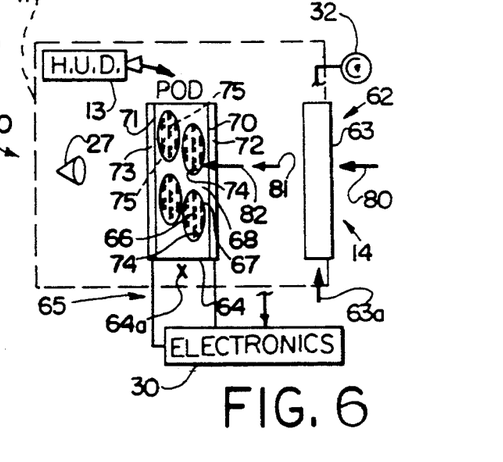
FIGS. 6 and 7 are schematic illustrations of a third embodiment according to the invention using a variable polarizer device, which is shown, respectively, in deenergized light blocking mode and energized light transmitting mode, in the goggles and a fixed polarizer in the visor.
Figure 7:
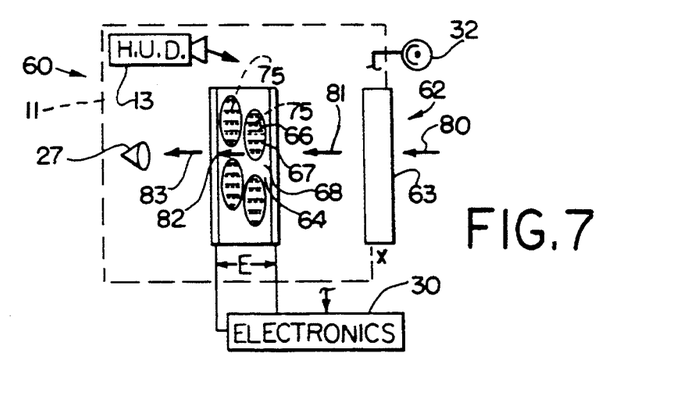

Turning briefly to FIGS. 6 and 7, another embodiment of the invention is illustrated in the form of the combination of a helmet, eye protection apparatus, and heads up display which make up a system 60. The system 60 is similar in parts and function to the system 10 described above. The differences are described below.

In the system 60 the helmet 11 and heads up display 13 are as described above. The eye protection apparatus 62 is different from the above-described embodiments. The eye protection apparatus 62 primarily includes the following parts: a first member 63 for selectively passing incident electromagnetic energy toward the wearer's eyes as a function of a prescribed characteristic of such electromagnetic energy; a second member 64 for selectively passing incident electromagnetic energy passed by the first member toward the wearer's eyes as a function of a prescribed characteristic of such electromagnetic energy; and a device 65 for changing a characteristic of at least one of the first and second members to increase and/or to decrease the amount of electromagnetic energy that can be passed thereby. In the illustrated embodiment it is the second member which is able to have such characteristic changed. It is noted here that in the embodiment of the invention illustrated in FIG. 8 the first member is able to have such characteristic changed; and in the embodiment of the invention illustrated in FIG. 9 both the first and second members are able to have such characteristic changed.

In the system 60 the prescribed characteristic of the electromagnetic energy is polarization, preferably plane polarization; the first member 63 is a plane polarizer; and the second member 64 is controlled variable polarizer, preferably a controlled variable plane polarizer liquid crystal device. Examples of such a controlled variable polarizer are presented in U.S. patent applications Ser. No. 07/259,951, filed Oct. 19, 1988, and Ser. No. 07/261,045, filed Oct. 21, 1988, the entire disclosures of which hereby are incorporated by reference. The characteristic of the second member 64 that can be changed is the efficacy, effectiveness or efficiency of the member 64 as a polarizer. The first member 63 may be part of the helmet visor 14 and the second member 64 may be part of the lens for the goggles 25, as above.

For convenience in FIGS. 6 and 7 the first polarizer 63 is shown having an axis of polarization 63a that is vertical and parallel to the plane of the drawing, and the axis of polarization 64a of the variable polarizer 64 is into the plane of the drawing (i.e., crossed relative to the axis 63a). However, it will be appreciated that the directions of the polarizers 63, 64 may be rotated 90 degrees relative to those illustrated if desired or to some other orientation; but preferably the polarizers 63, 64 are maintained in crossed or at least partly crossed relation so as to provide for blocking of at least some light from the eyes 27 under the desired conditions.

Referring to the variable polarizer 64, it includes liquid crystal material 66 contained in volumes 67, preferably elongate volumes, which are formed in a containment medium 68. The axis of elongation of such volumes 67 determines the preferred direction of alignment of the liquid crystal structure in the absence of a prescribed input, such as an applied field, e.g., an electric field or a magnetic field. The volumes 67 preferably are operative by surface interaction with the liquid crystal material 66 to effect generally parallel alignment of the liquid crystal structure with respect to the major, long or elongate axis of the volume. Preferably, the length of each volume 67 is appreciably greater than the diameter of the volume, and preferably a number of the volumes are interconnected. The greater the aspect ratio of the volume, i.e., the ratio of length to diameter or width, the greater will be the generally linear alignment of the liquid crystal structure.

Although only four volumes 67 are shown in the containment medium 68, it will be appreciated that the illustrations in FIG. 6 and 7 are greatly magnified from the actual physical size of a controlled variable liquid crystal optical polarizer within which four such volumes would be included, and in fact there would be many such volumes in the containment medium forming the variable polarizer 64. As an example, the larger diameter or width of such volumes, e.g., as is measured in the horizontal direction across a volume in FIG. 6, might be on the order of from about one-half micron to about seven microns; and the axial length of such volume along the axis would be several times, as is illustrated about two to five times the diameter. However, while it is preferred that the elongation of the volumes be maximized, the invention would operate with smaller amount of elongation or aspect ratio or a larger amount of elongation or aspect ratio than that mentioned here. Also, the dimensions are exemplary only and other dimensions may be employed.

The containment medium 68 preferably forms a three-dimensional matrix of the volumes 67, wherein the volumes effectively are closed to the environment externally of the containment medium. The volumes may be in a single layer or in multiple layers; in FIGS. 6 and 7 two layers are shown for simplicity.

Preferably on the surfaces 70, 71 of the containment medium 68 there are respective transparent electrodes 72, 73. Exemplary transparent electrodes may be formed of indium tin oxide, as is well known. Electrodes 72, 73 are used to apply a prescribed input, specifically an electric field, across the liquid crystal material 66. If the energy of such electric field is adequate to overcome the surface interaction of the wall 74 with the liquid crystal 66, the liquid crystal structure tends to align generally in parallel with such electric field in the manner illustrated in FIG. 7. If the applied electric field is less than that necessary to obtain complete alignment in the manner illustrated in FIG. 7, then the liquid crystal structure would tend to be oriented at an angle that is not generally parallel to the volume axis or to the direction of the electric field, i.e., the liquid crystal would be partly oriented in the direction of the electric field but still would be partly oriented due to the described surface interaction. To accomplish the foregoing alignment characteristics with respect to electric field, it is necessary that the liquid crystal material 66 have positive dielectric anisotropy. The electronics 30 may be employed to provide such electric field, as may be desired or required (e.g., under control of the sensor 32), in the form of an AC or DC voltage. Accordingly, the electronics 30 in association with electrical leads 30a, 30b and electrodes 72, 73 provide the function of the changing device 65.

Included with the liquid crystal material 66 is pleochroic dye 75. The pleochroic dye is represented by a dashed line in the respective volumes 67; only one or two such dashed lines are shown to avoid cluttering the drawing, but it will be appreciated that an appropriate quantity of liquid crystal material and of pleochroic dye would be contained in respective volumes to carry out the operation of the controlled variable polarizer 64 in the manner described. The pleochroic dye, sometimes referred to as dichroic dye, may be neutral density or may have color characteristics. The pleochroic dye 75 is operative to affect polarization of light incident thereon. The pleochroic dye 75 has the characteristic to function in guest-host relationship with the liquid crystal material 66. Accordingly, the structural orientation or alignment of the pleochroic dye will follow generally the structural orientation of the liquid crystal material. Although pleochroic dye is preferred, it will be appreciated that other means for affecting polarization of light as a function of orientation thereof and having a structural orientation that can be controlled by liquid crystal material may be utilized in accordance with the invention. Also, it is possible that the liquid crystal material 66 may function to affect polarization in the same way as the pleochroic dye 75 does, but without using the pleochroic dye. Therefore, throughout the patent application it will be appreciated that reference to pleochroic dye includes reference to equivalent means (even using solely the liquid crystal material itself) for carrying out the polarization function of the described pleochroic dye in the operative manner summarized below.

Operation of the controlled variable liquid crystal optical polarizer 64 now is summarized. For this summary, the liquid crystal material 66, the containment medium 68, the electrodes 72, 73, and the pleochroic dye 75 are colorless. The liquid crystal material 66, containment medium 68, and electrodes 72, 73 are transparent. Unpolarized light 80 is incident on plane polarizer 63; plane polarized light 81 passing through polarizer 63 has vertical polarization (in the direction of the arrow 63a). Light 82 travels in controlled variable polarizer 64. (In FIG. 6 such light 82 stops in polarizer 64. In FIG. 7 at least some of light 82 passes through polarizer 64 emanating as light 83 which passes to the viewer's eyes 27.

Assuming plane polarized light 81 is incident on the polarizer 64 and the liquid crystal 66 and dye 75 are structurally aligned in the manner illustrated in FIG. 6, light 82 will be attenuated and possibly entirely blocked, as is represented in FIG. 6. The pleochroic dye 75 tends to absorb that incident light of which the electric vector is vibrating in a plane that is parallel to the direction of the structural alignment of the pleochroic dye; sometimes it is said that such electric vector is absorbed. Since the plane polarized light 81 has its electric vector vibrating in such direction of alignment of the pleochroic dye 75, such light is absorbed or blocked.

In contrast, the electric vector of the incident light which is vibrating in a direction that is orthogonal to the alignment direction of the pleochroic dye will not be absorbed and, in fact, will be transmitted by the polarizer 64. However, since the light 81 preferably is plane polarized with a polarization direction that is parallel to the direction of alignment of the pleochroic dye 75, no light (or at least only attenuated light) is transmitted by the polarizer 64.

Preferably the pleochroic dye 75 does not absorb light that is incident thereon in a direction of propagation parallel to the axis or structure thereof. Such alignment occurs when the appropriate field input is supplied or applied across the controllable variable polarizer liquid crystal device 64, which is shown in FIG. 7. Therefore, as is illustrated in FIG. 7, the incident plane polarized light 81 would be transmitted through the polarizer 64 as light 82 and will exit the polarizer 64 as plane polarized light 83, which has a polarization direction that is parallel to the direction of polarization of light 81. In fact, when such controllable variable polarizer liquid crystal device 64 is in the condition illustrated in FIG. 7, it would not be operating as a polarizer, as the structure of the liquid crystal material 66 and the pleochroic dye 75 are aligned generally in parallel with the direction of propagation of light 82 therethrough.

In view of the foregoing, then, it will be appreciated that the polarization characteristics or effectiveness of the controlled variable polarizer 64 will be a function of the alignment characteristics of the pleochroic dye 75 in the volumes 67. The polarizer 64 will provide substantial plane polarization effectiveness, e.g., the same as a conventional fixed plane polarizer, when no electric field is applied across the liquid crystal material 66, may have substantially no polarization characteristic when an electric field adequate to achieve the alignment depicted in FIG. 7 is applied to the liquid crystal, and may have a partially polarization characteristic, i.e., providing some degree of polarization, but still permitting transmission of some unpolarized light (or light having an electric vector that is in the direction of the axis of the volumes 67) when there is applied a mid-range electric field that is large enough to cause some (or even all) of the liquid crystal (and pleochroic dye) structure to align out of parallel with the axis of the volumes 67 but not quite fully in the orthogonally aligned relation illustrated in FIG. 7.

Operation of the eye protection apparatus 62 of the apparatus 60 of FIGS. 6 and 7 will be similar to operation of the apparatus 10 described above in FIGS. 1–3. When it is desired to have light 80, e.g., light carrying image information from the scene or view outside an aircraft, pass through the helmet 11 visor 14 to the eyes 27, the controllable variable polarizer 64 has electric field E applied across the liquid crystal 66 by the changing device 65 (including electronics 30), as is seen in FIG. 7. Plane polarized light 81 transmitted through the polarizer 63 then passes as light 82 through the variable polarizer 64 and is received as light 83 by the eyes 27. However, when the sensor 32 senses excessive light input, e.g., relatively intense laser light, the electronics 30 in the changing device reduces or eliminates the electric field E to the controllable variable polarizer 64, which then increases the polarizing effectiveness or polarizing efficiency thereof. The crossed relationship of the fixed polarizer 63 and the variable polarizer 64 then reduces the intensity of laser light reaching the eyes 27 or substantially completely blocks such laser light from reaching the eyes. In either operative mode of the eye protection apparatus 62, the heads up display 13 may be operative to project images at the space 53 on the visor for viewing by the eyes 27. An advantage of the eye protection apparatus 62 is that since the controllable variable polarizer 64 operates in a non-polarizing mode when the eye protection apparatus 62 is not blocking light 82, such polarizer will not affect, i.e., attenuate, the image formed at the area or space 53 by the heads up display, thus permitting increased brightness of the heads up display image as viewed by the eyes 27 when the apparatus 62 is not in light blocking mode. It will, of course, be appreciated that whenever a polarizer is placed in an optical path, unpolarized light incident on such polarizer will be reduced in intensity by about fifty percent due to the filtering effected by the polarizer.

Figure 8:
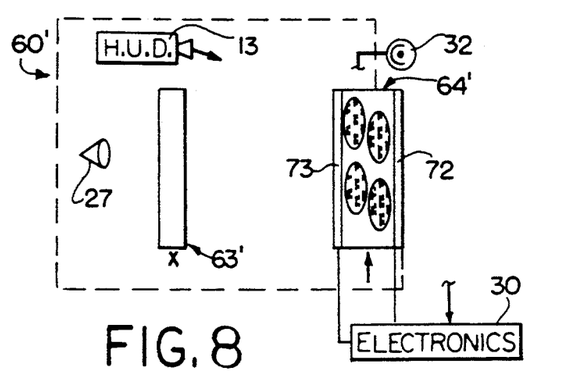
FIG. 8 is a schematic illustration of a fourth embodiment (in deenergized light blocking mode) similar to that shown in FIGS. 6 and 7, except that the variable polarizer is associated with the visor and the fixed polarizer is in the goggles.

Turning briefly to FIG. 8, another embodiment of the invention is illustrated in the form of the combination of a helmet, eye protection apparatus, and heads up display which make up a system 60'. The system 60' is similar in parts and function to the system 60 described above except that the relative positions in the optical path of the eye protection apparatus 62' of the polarizer 63' and the controllable variable polarizer 64' are reversed. In FIG. 8 the parts that are identified by primed reference numerals correspond to parts identified by the same unprimed reference numerals described elsewhere herein. Therefore, the description of such parts and operation thereof is presented above. An advantage of the system 60' relative to the system 60 is that since all light from the heads up display 13 will have to pass through the fixed polarizer 63', the intensity of such light will not change as the polarization effectiveness of the controllable variable polarizer 64' changes.

Figure 9:
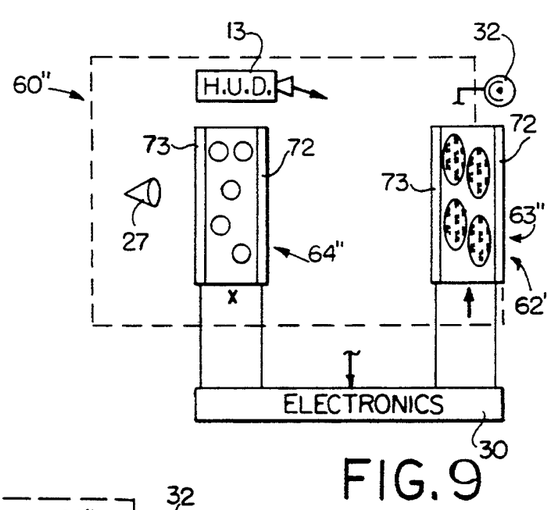
FIG. 9 is a schematic illustration of a fifth embodiment (in deenergized light blocking mode) using two variable polarizers.

Referring, now, to FIG. 9, another embodiment of the invention is illustrated in the form of the combination of a helmet, eye protection apparatus, and heads up display which make up a system 60". The system 60" is similar in parts and function to the system 60 described above except that both of the crossed polarizers 63" and 64" are of the controllable variable polarizer type, as the variable polarizer 64, 64' described above. In FIG. 9 the parts that are identified by double primed reference numerals correspond to parts identified by the same primed and unprimed reference numerals described elsewhere herein. Therefore, the description of such parts and operation thereof is presented above. An advantage of the system 60" relative to the systems 60 and 60' is that since both crossed polarizers 63" and 64" can be controlled so as to be non-polarizing, when both are in such non-polarizing operative mode, substantially all light incident on the visor 14 from outside the visor will be directed to the eyes 27 substantially without attenuation; therefore, the brightest viewing possible is achieved. However, when it is desired to reduce the intensity of light to the eyes 27 derived from the light 80" incident on the visor 14, either or both of the controllable variable polarizers may be appropriately operated to increase the polarization effectiveness thereof.

In the system 60" the changing device 65", including electronics 30, would be responsive to the output from the sensor to adjust the polarization effectiveness of one or both polarizers 63", 64". For example, if the intensity of light incident on the sensor 32 were below a first relatively low threshold level, both polarizers 63", 64" would be in non-polarizing mode. If the intensity of light exceeded such first threshold but were less than a second higher threshold, then one or the other of the polarizers 63", 64" may be made substantially fully effective polarizing, but not both; or both may be made partially polarizing effective but not totally polarizing effective. Finally, if the light intensity were to exceed the second threshold, then both polarizers 63", 64" would be made substantially fully polarizing effective to block light from reaching the eyes. The particular form of the electronics 30 as used in the system 60" may be the same as that illustrated in FIG. 2 but modified to accommodate the above-described operative functions with appropriate amplifiers, threshold detectors, etc.

Figure 10:
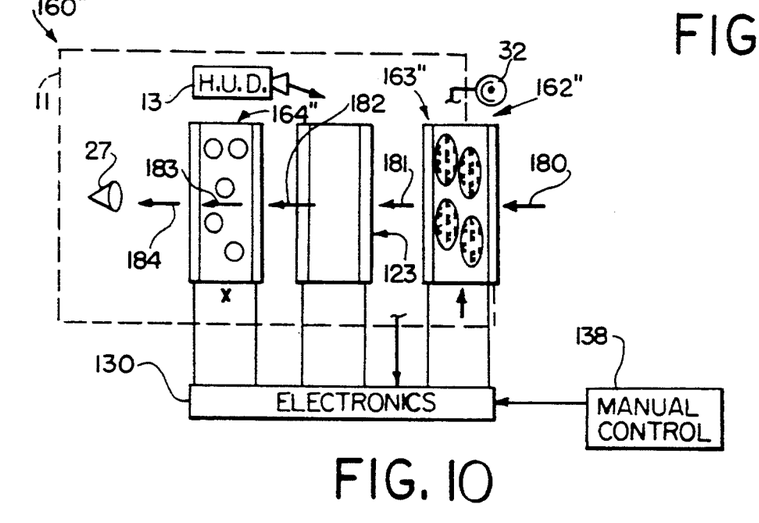
FIG. 10 is a schematic illustration of a sixth embodiment using plural variable polarizers, shown in operative mode to block light as determined by an optical rotator.

In FIG. 10 is a further embodiment of the invention in the form of the combination of a helmet 11, eye protection apparatus 12, and heads up display 13 which make up a system 160". The system 160" is similar in parts and function to the system 60" described above except that in addition to using both of the crossed controllable variable polarizers 63" and 64" there also is a changing device 123, which may be the same or similar to the changing device 23 described above, such as a surface mode liquid crystal type of birefringent controllable variable optical retarder. Accordingly, the variable polarizers 163", 164" may be fully non-polarizing; then, regardless of the operation of the changing device, substantially full light transmission from outside the eye protection apparatus 162" to the eyes 27 is possible. When conditions warrant possible use of the eye protection apparatus 162" to block high intensity light from the eyes 27, the polarizers 163" and 164" may be manually adjusted by the manual control 138 to partial or full polarization effectiveness, and then under control of the sensor 32 and the electronics 130, which may include circuitry of the type illustrated at 30 in FIG. 2, the retarder 123 may be operated or not to rotate the plane of polarization of polarized light thereby to block undesired high intensity electromagnetic energy from the eyes 27.

Summarizing, then, in operation of the system 160", when maximum light intensity is to be transmitted to the eyes 27, both polarizers 163" and 164" are receiving electric field E to be non-polarizing; and light 180 passes as light 181, 182, 183, and 184 to the eyes 27; the light 184 is not substantially different in intensity from the intensity of light 180. When it is desired to be prepared for fast acting blocking, the polarizers 163", 164" may be set to full polarizing effectiveness and the retarder/rotator or changing device 123 is set to rotate the plane of polarization (as in the apparatus 12 of FIGS. 1-3). Then, upon the occurrence of high intensity electromagnetic energy as detected by the sensor 32, the electronics 130 would cause the changing device 123 to stop rotating the plane of polarization, whereupon light 180, 181, and 182 will be transmitted, as is shown, and in the polarizer 164" light 183 will be blocked so that light 184 will not reach the eyes 27. Meanwhile, regardless of the operation of the various portions of the eye protection apparatus 162", the heads up display 13 will work in the manner described elsewhere herein.

Figure 11:
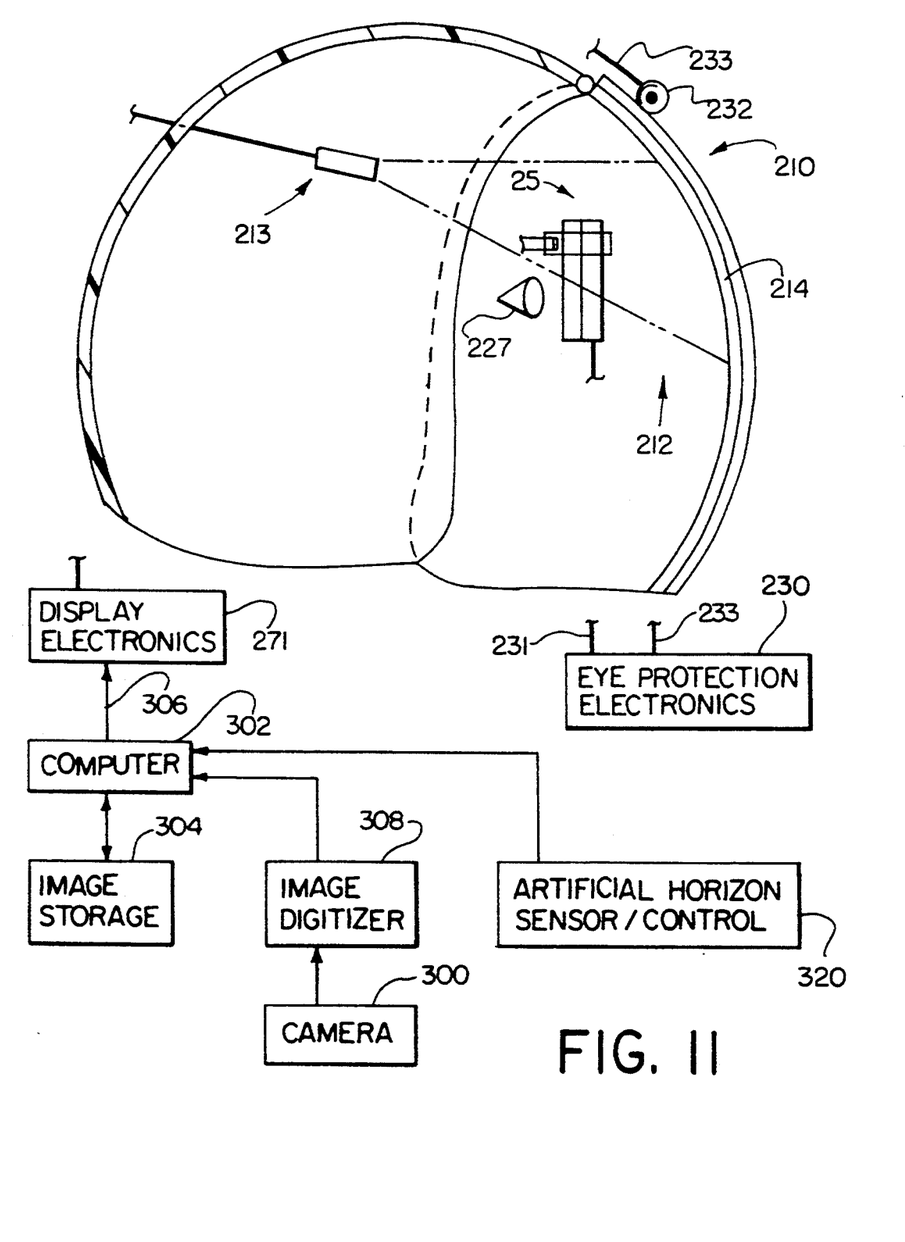
FIG. 11 is a schematic illustration of a seventh embodiment using an artificial image generator.

Referring to FIG. 11, in addition to the foregoing, the invention relates to a safety feature for use in aircraft and/or other vehicles to provide artificial information to enable or to facilitate operating of the aircraft and/or other vehicle during the period that the operator's eyes are being protected from specified electromagnetic energy. In FIG. 11 a modified system 210 is illustrated. In the modified system 210 there is a helmet which is represented by a visor 214, an eye protection apparatus 212, and a heads up display 213, all generally as were described above with reference to the above-identified drawings and similar reference numerals (without the "200's" prefix). Accordingly, eye protection electronics 230, photosensor 232, etc. are employed in the modified system, and a display electronics 251 also is employed in the modified system 210.

Operation of the modified system 210 enables the individual whose eye 227 is represented in the drawing of FIG. 11, for example, still to operate the aircraft and/or other vehicle intended to be operated even when eye protection function is in operation to block input of light from outside the visor reaching the eyes 227. Such capability is provided by using the heads up display 213 to project for viewing by the operator (pilot, for example) an image that can be relied on to continue operating the aircraft and/or other vehicle. Such image may be, for example, an image, whether real, stored, recreated (e.g., cartoon-like), etc., that represents what it is expected would timely be seen if one were to look outside the vehicle. Alternatively, such image may be, for example, an artificial horizon image that would enable a pilot to continue flying an aircraft for a period of time even though other optical input to the pilot's eyes, i.e., of the real space outside the aircraft, were not viewable.

To produce such an image referred to just above, the modified system 210 includes a camera 300, such as a television camera, an already existing gun camera located on an aircraft, etc., a computer 302 for computing expected visual information, a memory 304, for example for storing image information from the camera, and a connection 306 to the display electronics 251 for driving the heads up display 213. If desired, an image digitizing circuit 308 of conventional type may be used to convert the image information from the camera 300 to a digital representation thereof for operation thereon and/or storage thereof by the computer 302. Alternatively, a digital type of image information may be generated by the camera 300 itself for storage and subsequent use as below.

Preferably using the camera 300, image digitizer 308 (if used) and computer 302, sequential images of the real space, scene, etc. outside the aircraft are obtained and are stored in the memory 304. Such images may be supplied for storage in such memory on a first in first out basis so that the image information stored in memory constantly is updated with new information.

In the event that the eye protection system is operative to block light from reaching the pilot's eyes, the computer 302 is operative to rely on such stored image information and based thereon and on the altitude, speed, and direction of the aircraft to compute what the image of such real space would appear to the pilot then and at some time in the future, for example, for several seconds or minutes. The computer is operable, then, to provide to the heads up display electronics 251 driving information to cause the heads up display to project the scene or real space view that would be expected to be seen if the pilot were able to see out through eye protection system. It is noted here that apparatus and software for effecting similar functions have been developed by NASA, e.g., for use in conjunction with movement of arms, hands, etc., of an individual using artificial motive means and computer means for storing, computing and projecting effective images to the operator. Other examples of apparatus and software to effect similar operation are employed in well known simulators, e.g., for aircraft and the like, such as those for training pilots.

For the purpose described, then, it is possible for the computer 302 to override the heads up display electronics 251 to produce the desired image that would enable the pilot to continue to fly the aircraft based on the generated information computed by the computer.

The image projected by the heads up display 213 may be of cartoon-like character that is of adequate clarity and information conveying format that the pilot would be able successfully to continue to operate the aircraft. Alternatively, other types of images may be produced by such computer. Still further, it will be appreciated that desirably the duration that the computer is operative to produce such artificial computed real space image information should be adequate to match (approximately to equal) the time that is expected that the eye protection apparatus would be blocking a direct view of the real space outside of the aircraft.

Another alternative operation of the modified system 210 employs the artificial horizon equipment 320 of the aircraft. Such artificial horizon equipment is operative in the usual fashion to provide artificial horizon information to the conventional controls and/or displays of the aircraft. However, up the existence of a condition that the eye protection system is blocking light from the real space outside the aircraft, such artificial horizon information can be coupled via, received by or delivered to the computer 302 which then is able to include that information for projection by the heads up display 213 via the display electronics 251 either with the aforementioned real space image information or independently thereof. Based on such artificial horizon information, then, it is possible for the pilot at least to continue flying a level course until such time as the eye protection system becomes unblocking or at least for some time during the blocking operation of the eye protection system.

With the foregoing in mind, it will be appreciated that the modified system 210 of the invention as it is illustrated in FIG. 11 would be able to provide additional safety for the vehicle and operator thereof. Eye protection would be provided, and during the protection phase of operation of the system 210, image information would be projected by the system 210, especially by the cooperative effort of the computer 302 and the heads up display 213, to provide for a period of time information that would enable the operator to continue to operate the vehicle.

STATEMENT OF INDUSTRIAL APPLICATION

From the foregoing it will be appreciated that the present invention provides means to protect the eyes of a wearer from electromagnetic energy having prescribed characteristics while still allowing the use of the heads up display in a helmet system.

I claim:

1. A system for protecting the eyes of a wearer while permitting information to be conveyed to said eyes, comprising first polarizer means for selectively passing incident electromagnetic energy toward said eyes as a function of a polarization characteristic of said electromagnetic energy, second polarizer means for selectively passing incident electromagnetic energy passed by said first polarizer means toward said eyes as a function of the polarization of said electromagnetic energy, goggle means mountable over said eyes of said wearer and including changing means for rapidly changing the polarization characteristic of said incident electromagnetic energy received from said first polarizer means in response to an input to effect a cooperation between said first polarizer means and said second polarizer means to change the intensity of the electromagnetic energy received by said eyes, and heads up display means having an operative portion located to form an image between said first polarizer means and said second polarizer means and focused effectively at infinity with respect to said eyes of said wearer to provide said image viewable by said eyes of said wearer to convey information to said eyes of said wearer independently of the operative mode of said changing means, said heads up display means comprising projection means for projecting said image toward said first polarizer means for reflection to and viewing by said eyes.

2. The system of claim 1, wherein said first polarizer means and said second polarizer means comprises linear polarizers.

3. The system of claim 1, wherein said changing means comprises means for rotating the direction of polarization of electromagnetic energy transmitted from said first polarizer means prior to impingement on said second polarizer means.

4. The system of claim 3, wherein said changing means comprises a surface mode liquid crystal apparatus including liquid crystal material located between a pair of surfaces, means for applying an input to said liquid crystal material to affect alignment characteristics thereof, said liquid crystal material being operative to respond to such input by changing alignment of liquid crystal structure primarily proximate at least one of said surfaces without substantially affecting he alignment of at least some of the liquid crystal material located relatively remotely from said at least one of said surfaces.

5. The system of claim 1, wherein said first polarizer means is a plane polarizer having a polarization axis that is generally vertical to reduce glare.

6. The system of claim 1, wherein said first polarizer means and said second polarizer means are plane polarizers that are positioned such that the polarization axes thereof are crossed at ninety degrees.

7. The system of claim 1, wherein said first polarizer means and said second polarizer means are plane polarizers that are positioned such that the polarization axes thereof are relatively parallel.

8. The system of claim 1, wherein said first polarizer means and said second polarizer means are plane polarizers that are positioned such that the polarization axes thereof are partially crossed at other than ninety degrees.

9. The system of claim 1, further comprising means for sensing a condition requiring shielding, and means responsive to said means for sensing for operating said changing means to effect blocking of at least some of the incident electromagnetic energy from said eyes when said means for sensing senses a condition requiring shielding.

10. The system of claim 1, wherein at least one of said first polarizer means and second polarizer means is a variable polarizer comprising liquid crystal material contained in elongate volumes in a containment medium, wherein the axis of elongation of such volumes determines the preferred direction of alignment of the liquid crystal structure in the absence of a prescribed input thereby to determine the effective plane of polarization of light transmitted through said variable polarizer.

11. The system of claim 10, further comprising means for selectively supplying electric field to said variable polarizer as said prescribed input to change the polarization effectiveness thereof.

12. The system of claim 11, further comprising pleochroic dye in said liquid crystal material.

13. The system of claim 1, further comprising screen means on which said image is projected.

14. The apparatus of claim 13, further comprising a helmet to be worn on the head of said person and wherein said screen means comprises a visor of said helmet.

15. The system of claim 1, further comprising a helmet apparatus including a head piece to be worn on the head of said person and a visor mounted with respect to said head piece generally in the field of view of said eyes of said person, and wherein said goggles are intended to be worn by said person between said eyes of said person and said visor, said first polarizer means is mounted in proximity to said visor, said second polarizer means is mounted in proximity to said goggles, and said heads up display means forms said image to be viewed without regard to the optical relationship of said first polarizer means, said second polarizer means, and said changing means.

16. The helmet apparatus of claim 15, wherein said first polarizer means comprises part of said visor.

17. The helmet apparatus of claim 16, wherein said second polarizer means comprises part of said goggles.

18. The system of claim 1, further including screen means on which said image is projected for viewing by said eyes.

19. The system of claim 18, wherein said screen means comprises a surface between said first means and said second means.

20. The system of claim 19, wherein said screen means comprises a surface of said first polarizer means.

21. The system of claim 1, further comprising detector means for detecting a condition requiring a reduction of incident light to said eyes.

22. The system of claim 1, further comprising means for supplying said input to said changing means to affect the intensity of electromagnetic energy reaching said eyes in response to the intensity of electromagnetic energy incident on said first polarizer means.

23. The system of claim 1, wherein said changing means comprises a variable birefringent liquid crystal means.

24. A system for combining light from two sources, comprising
first means for selectively passing first incident electromagnetic energy, as a function of a first prescribed characteristic of said first electromagnetic energy, toward a merging area,
second means for selectively passing said first incident electromagnetic energy, which was passed by said first means to said merging area, as a function of said first prescribed characteristic of said passed electromagnetic energy, toward an area for viewing,
changing means for changing said first characteristic of said incident first electromagnetic energy in response to a function to effect a cooperation between said first means and said second means to change a second characteristic of said first electromagnetic energy received at said area for viewing,
means for directing second electromagnetic energy in a direction toward said first means for combining in a reflective manner with said first incident electromagnetic energy, which was passed by said first means, and wherein said second electromagnetic energy is generated by a heads up display generation means while said first electromagnetic energy is generated by neither said system nor said heads up display generation means.

25. The system of claim 24, wherein such electromagnetic energies are combined to form a spatially congruent view.

26. A system for providing artificial information to a vehicle operator while shielding the eyes of the operator to enable or to facilitate operating of the vehicle during the period that the operator's eyes are being shielded comprising an eye protection means selectively operable to shield the eyes of said operation, reflective heads up projection display means for displaying artificial information for viewing by the individual while the eyes are protected, and computer means for generating information for display by the heads up display means representative of the real space outside the vehicle while the eyes are shielded or representative of the attitude of the vehicle relative to said real space.

27. A method for providing artificial information to a vehicle operator while shielding the eyes of the operator from external electromagnetic energy to enable or to facilitate operating of the vehicle during the period that the operator's eyes are being shielded, comprising selectively operating a dynamic shield to shield the eyes of said operator and displaying, by a reflected projection, artificial information for viewing by said operator to enable said operator to operate the vehicle while the eyes are protected.

28. The method of claim 27, further comprising using a computer generating artificial information for displaying while the eyes are shielded.

29. The method of claim 27, wherein the vehicle includes artificial horizon information developing apparatus, and wherein displaying artificial information comprises displaying to said operator such artificial horizon information.

* * * * *